(12) United States Patent
Zhou et al.

(10) Patent No.: US 11,066,562 B2
(45) Date of Patent: Jul. 20, 2021

(54) ACRYLAMIDE-CONTAINING PHOTO ACTIVE CO-SOLVENTS

(71) Applicant: Hewlett-Packard Development Company, L.P., Spring, TX (US)

(72) Inventors: Zhang-Lin Zhou, San Diego, CA (US); Mazi Bar, Netanya (IL); Gregg A. Lane, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 140 days.

(21) Appl. No.: 16/334,482

(22) PCT Filed: Jan. 31, 2017

(86) PCT No.: PCT/US2017/015748
§ 371 (c)(1),
(2) Date: Mar. 19, 2019

(87) PCT Pub. No.: WO2018/143916
PCT Pub. Date: Aug. 19, 2018

(65) Prior Publication Data
US 2019/0211217 A1    Jul. 11, 2019

(51) Int. Cl.
| | | |
|---|---|---|
| *C09D 11/03* | (2014.01) | |
| *C09D 11/033* | (2014.01) | |
| *C09D 11/101* | (2014.01) | |
| *C07C 233/09* | (2006.01) | |
| *C09D 11/38* | (2014.01) | |
| *C07C 233/16* | (2006.01) | |
| *C09D 11/102* | (2014.01) | |
| *C07C 233/20* | (2006.01) | |

(52) U.S. Cl.
CPC .......... *C09D 11/033* (2013.01); *C07C 233/09* (2013.01); *C07C 233/16* (2013.01); *C07C 233/20* (2013.01); *C09D 11/101* (2013.01); *C09D 11/102* (2013.01); *C09D 11/38* (2013.01)

(58) Field of Classification Search
CPC ... C07C 233/20; C07C 233/16; C09D 11/033; C09D 11/38; C09D 11/102; C09D 11/101
See application file for complete search history.

(56) References Cited

U.S. PATENT DOCUMENTS

| | | | | |
|---|---|---|---|---|
| 4,482,354 A | * | 11/1984 | Sung | C10L 1/08 44/405 |
| 4,683,272 A | * | 7/1987 | Cuscurida | C08F 299/022 521/137 |
| 5,317,080 A | * | 5/1994 | Arimatsu | C08F 20/54 430/283.1 |
| 5,589,522 A | * | 12/1996 | Beach | C08F 8/32 523/160 |
| 5,709,737 A | | 1/1998 | Malhotra et al. | |
| 7,759,454 B2 | * | 7/2010 | Falk | C07C 231/02 528/422 |
| 8,317,312 B2 | * | 11/2012 | Ooishi | C09D 4/06 347/100 |
| 8,905,534 B2 | * | 12/2014 | Amao | B41J 2/2107 347/100 |
| 9,034,940 B2 | | 5/2015 | Kida et al. | |
| 9,532,010 B2 | * | 12/2016 | Baumann | A61B 1/00179 |
| 2004/0209976 A1 | | 10/2004 | Nakhmanovich et al. | |
| 2006/0252884 A1 | * | 11/2006 | Falk | C07C 231/02 525/86 |
| 2008/0146381 A1 | * | 6/2008 | Kondos | C08G 18/10 473/378 |
| 2013/0337237 A1 | | 12/2013 | Wu et al. | |

FOREIGN PATENT DOCUMENTS

| | | |
|---|---|---|
| WO | 2009079647 | 6/2009 |
| WO | 2016122454 | 8/2016 |

OTHER PUBLICATIONS

International Search Report dated Oct. 26, 2017 for PCT/US2017/015748, Applicant Hewlett-Packard Development Company, L.P.

\* cited by examiner

*Primary Examiner* — Sanza L. McClendon
(74) *Attorney, Agent, or Firm* — Thorpe North & Western LLP

(57) ABSTRACT

The present disclosure is drawn to an acrylamide-containing photo active co-solvent, including a bis-tris propane co-solvent or a polypropylene oxide amine co-solvent modified with an acryloyl group to form the acrylamide-containing photo active co-solvent.

19 Claims, 1 Drawing Sheet

BASE COMPOUND 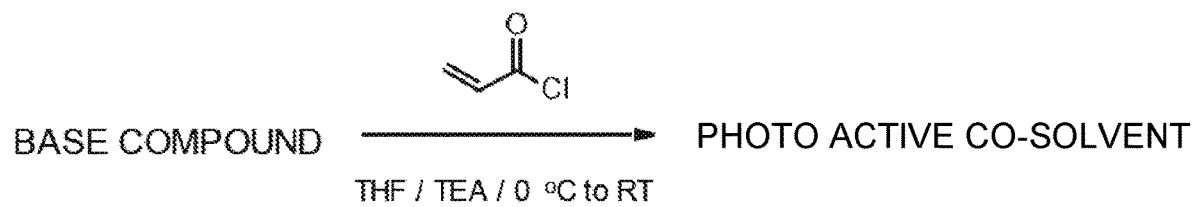 PHOTO ACTIVE CO-SOLVENT

ACRYLAMIDE-CONTAINING PHOTO ACTIVE CO-SOLVENTS

BACKGROUND

Recently, curing of ink by radiation, and in particular ultraviolet (UV) curing, has become popular. UV curable ink can be cured after printing by application of UV light. Typically, UV curable inks include monomers that form polymers by free radical polymerization. The growing end of each polymer chain is a radical that reacts with additional monomers, transferring the radical to the end of the chain as each monomer is added. A photo initiator can be used to form first radicals to begin the polymerization process. The photo initiator can be capable of absorbing UV light to generate radicals to react with the monomers.

Two types of photo initiators can be used in UV curable compositions. Type I photo initiators are unimolecular photo initiators that undergo a hemolytic bond cleavage upon absorption of UV light, forming radicals. Type II photo initiators are bimolecular photo initiators. These are used as a system of a photo initiator with a synergist, which can together form radicals upon exposure to UV light. Some Type II photo initiators react by hydrogen abstraction from the synergist to the photo initiator.

BRIEF DESCRIPTION OF THE DRAWING

FIG. 1 provides an example of a general formula depicting the conversion of a base compound to a photo active co-solvent by reaction with an acryloyl halide, such as an acryloyl chloride; and FIG. 2 provides an example method of making a photo curable ink in accordance with the present disclosure.

DETAILED DESCRIPTION

The inkjet printing industry uses various types of inks, such as oil-based inks, solvent-based (non-aqueous) inks, water-based (aqueous) inks, and solid inks which are melted in preparation for dispensing. Solvent-based inks are fast drying, and as a result, are widely used for industrial printing. When solvent-based inks containing binders and other ingredients are jetted onto a substrate, the solvent(s) partially or fully evaporate from the ink, leaving the binder and other ingredients such as pigment particles on the printed substrate in the form of a dry film. During the drying process, the solvents, which are often volatile organic compounds (VOC), emit vapors, and therefore, can pollute the environment. The amount of pollution produced can increase greatly with higher printing speeds or for wide format images, where large amounts of ink are deposited onto a substrate.

As a result of this and other concerns, efforts related to preparing inks that are environmentally friendly have moved some research in the direction of water-based inks. However, radiation curable (or photo curable) water-based ink compositions are noticeably limited among available options of photo active co-solvents due to their specific formulation properties. For example, even though one can use dispersions of photo initiators along with a dispersant, there can be crystallization issues that get introduced at high concentrations in the ink. Thus, it would be desirable to develop water soluble or water compatible photo active materials, including those that may also be physically and/or chemically stable in photo curable ink formulations.

One such photo active material that can be used is a photo active co-solvent that is compatible in water-based systems, and which can participate in polymerization under exposure to UV energy. The photo active co-solvent described herein can be admixed with water and other co-solvent, or as part of a co-solvent package. These photo active co-solvents can be water soluble and/or water stable in a basic environment, and furthermore, can be reactive in photo curable ink formulations, for example. Their stability can be in part due to the presence of an acrylamide linkage. In addition to being stable in the ink, these photo active co-solvents can be cross-linkable under UV-LED exposure, making them non-VOC, and contributing to the high durability of inks in which these co-solvents are included. In one example, these photo active co-solvents can work together with photo active binders to provide enhanced durability in some cases than with respect to the use of the photo curable binder alone.

Accordingly, the present disclosure is drawn to an acrylamide-containing photo active co-solvent, which can include a bis-tris propane co-solvent or a polypropylene oxide amine co-solvent modified with an acryloyl group to form the acrylamide-containing photo active co-solvent. In one example, the polypropylene oxide amine can also include polyethylene oxide groups. Example structures are shown at Formulas I to VI below. In other examples, the acrylamide-containing photo active co-solvent can include multiple acrylamide groups. In another example, the acrylamide-containing photo active co-solvent can include a secondary amide. In still another example, the acrylamide-containing photo active co-solvent can include a tertiary amide.

The present disclosure also provides a photo curable ink. The ink can include a photo reactive binder; a photo initiator; a co-photo initiator, a synergist, or combination thereof; a colorant; and a liquid vehicle including water and a bis-tris propane co-solvent or a polypropylene oxide amine co-solvent reacted with an acryloyl group to form an acrylamide-containing photo active co-solvent. In one example, the acrylamide-containing photo active co-solvent can include a secondary amide. In another example, the acrylamide-containing photo active co-solvent can include a tertiary amide. In yet another example, the acrylamide-containing photo active co-solvent can include multiple acrylamide groups.

In another example, a method of preparing a photo curable ink can include mixing a photo reactive binder; a photo initiator; a co-photo initiator, a synergist, or combination thereof; a colorant; and a liquid vehicle including water and an acrylamide-containing photo active co-solvent including a bis-tris propane co-solvent or a polypropylene oxide amine co-solvent reacted with an acryloyl group.

In further detail as it relates to the photo active co-solvents of the present disclosure, these co-solvents can be prepared by reacting a base compound co-solvent with an acryloyl halide (e.g., acryloyl chloride) to form a photo active co-solvent in accordance with the present disclosure, as shown at FIG. 1.

Example of Photo Active Co-solvents that can be prepared in accordance with FIG. 1 include the following:

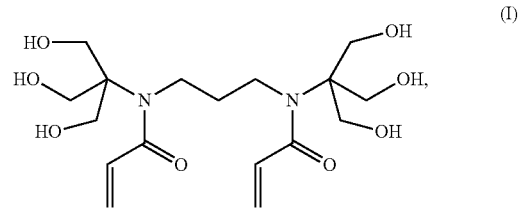

-continued

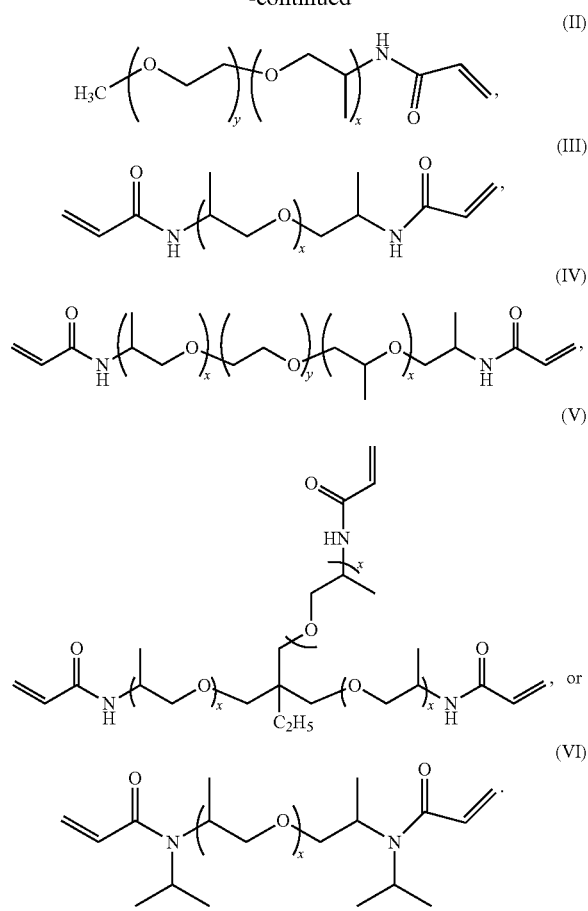

where each x can be independently from 1 to 70, and y can be from 1 to 40. In one example, each x can independently be from 2 to 30 or from 4 to 10. In another example, y can be from 2 to 30 or from 4 to 10.

Scheme 1 shows the preparation of Photo Active Co-solvent I from the commercially available starting material bis-tris propane by reaction with acryloyl chloride in THF and TEA at 0° C.

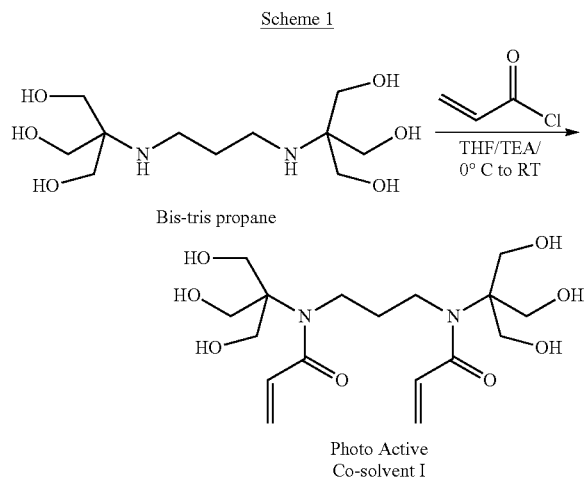

Schemes 2 through 6 show six additional examples of preparing Photo Active Co-solvents (2-6), where the Starting Base Compound are based on Jeffamine® polyetheramines, available from Huntsman Chemical. Jeffamine® polytheramines contain primary amino groups attached to the end of various polyether backbones. The polyether backbones are normally based on polypropylene oxide (PPO), but can also further include polyethylene oxide (PEO). These compounds are generally water soluble. Introduction of curable acryloyl groups (from an acryloyl halides) into these Jeffamine® base compounds result in various Photo Active Co-solvents.

Scheme 2 depicts the synthesis of a Photo Active Co-solvent II (JA-MA) from Jeffamine® M by the reaction with acryloyl chloride in THF/TEA at 0° C., followed by treatment of sodium bicarbonate.

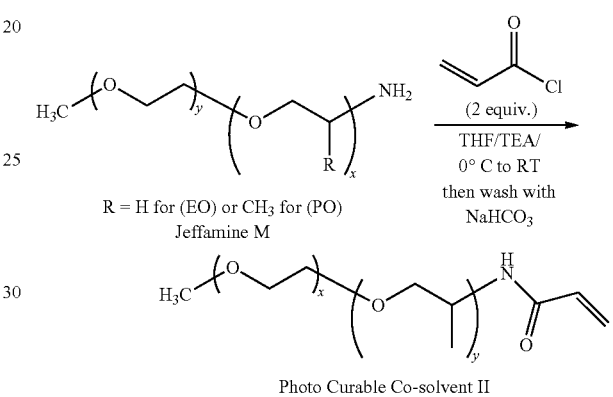

In Scheme 2, x can be from 1 to 70, and y can be from 1 to 40. In one example, x can be from 2 to 30 or from 4 to 10. In another example, y can be from 2 to 30 or from 4 to 10.

Scheme 3 depicts the synthesis of a Photo Active Co-solvent III (JA-DDA) from Jeffamine® D by the reaction with acryloyl chloride in THF/TEA at 0° C., followed by treatment of sodium bicarbonate.

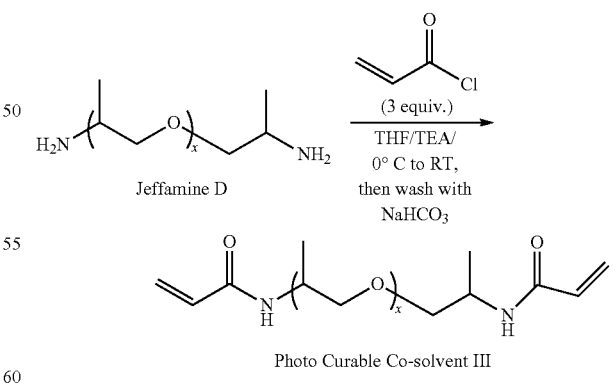

In Scheme 3, x can be from 1 to 70. In one example, x can be from 2 to 30 or from 4 to 10.

Scheme 4 depicts the synthesis of a Photo Active Co-solvent IV (JA-900 DA) from Jeffamine® JA-900 by the reaction with acryloyl chloride in THF/TEA at 0° C., followed by treatment of sodium bicarbonate.

Scheme 4

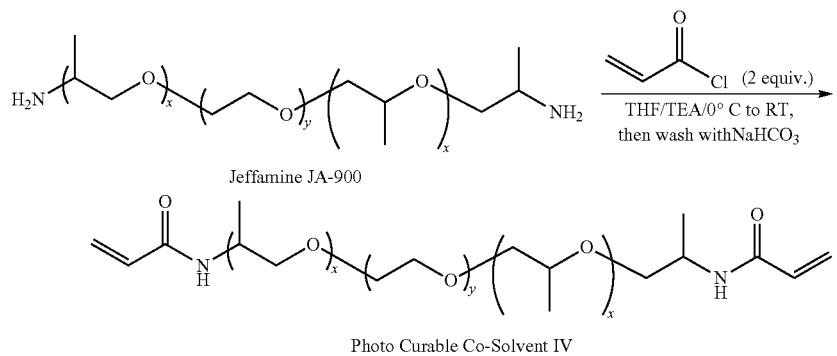

Photo Curable Co-Solvent IV

In Scheme 4, each x can independently be from 1 to 70, and y can be from 1 to 40. In one example, each x can independently be from 2 to 30 or from 4 to 10. In another example, y can be from 2 to 30 or from 4 to 10.

Scheme 5 depicts the synthesis of a Photo Active Co-solvent V (JA-T-403 TA) from Jeffamine® JA-T-403 by the reaction with acryloyl chloride in THF/TEA at 0° C., followed by treatment of sodium bicarbonate.

Scheme 5

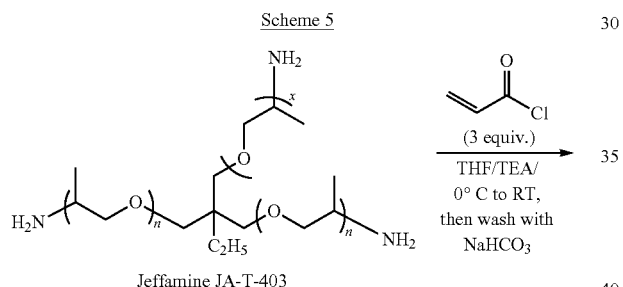

Photo Curable Co-solvent V
(x+y+z = 5-6)

In Scheme 5, each x can independently be from 1 to 70. In one example, each x can independently be from 2 to 30 or from 4 to 10.

Scheme 6 depicts the synthesis of a Photo Active Co-solvent VI (JA-XTJ DA) from Jeffamine® XTJ by the reaction with acryloyl chloride in THF/TEA at 0° C., followed by treatment of sodium bicarbonate.

Scheme 6

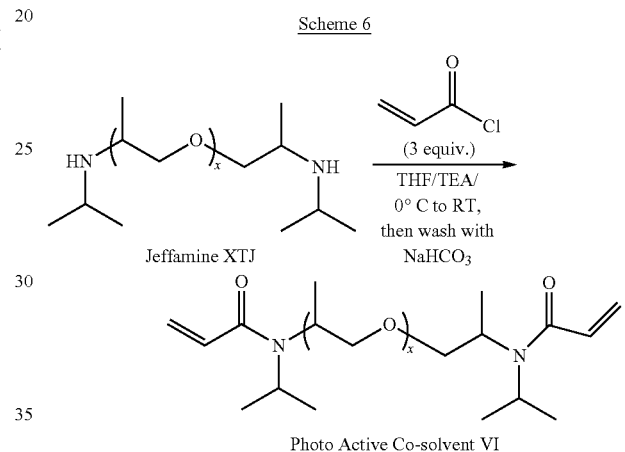

Photo Active Co-solvent VI

In Scheme 6, x can be from 1 to 70. In one example, x can be from 2 to 30 or from 4 to 10.

The present disclosure also extends to photo curable inks, such as UV curable inks including LED curable inks. In some examples, a photo curable ink can include a photo reactive binder (such as a UV curable or LED curable binder), a photo active co-solvent, a photo initiator, a co-photo initiator and/or a synergist, a colorant, a co-solvent, and water. The photo active co-solvent(s) can be as described herein, and as exemplified in Formulas I to VI, and in Schemes 1 to 6. As mentioned, these co-solvents can be water stable in a basic environment, reactive in photo curable ink formulations, cross-linkable under UV-LED exposure, and contribute to the high durability of photo curable inks generally. In one example, these photo active co-solvents can work together with photo active binders to provide enhanced durability compared to inks without these photo active co-solvents, particularly is it may relate to scratch resistance.

With respect to the photo reactive binder, these materials can include a UV or LED curable polyurethane (cPUD) and/or hydrophobic radiation-curable monomers. In one example, the UV reactive binder can include a water dispersible (meth)acrylated polyurethane, such as NeoRad® R-441 by NeoResins (Avecia). Other examples of UV reactive binders can include Ucecoat® 7710, Ucecoat® 7655 (available from Cytec), Neorad® R-440, Neorad® R-441, Neorad® R-447, Neorad® R-448 (available from DSM NeoResins), Bayhydrol® UV 2317, Bayhydrol® UV VP LS 2348 (available from Bayer), Lux 430, Lux 399, Lux 484 (available from Alberdingk Boley), Laromer® LR 8949, Laromer® LR 8983, Laromer® PE 22WN, Laromer® PE 55WN, Laromer® UA 9060 (available from BASF), or combinations thereof.

The photo initiators or co-photo initiators can act as a Type I or a Type II photo initiator. Thus, the photo curable ink can include a sensitizer component and/or a synergist. In the case of the synergist, an amine synergist can be used, for example. The photo initiator and synergist together can generate radicals during photo curing, such as with UV curing or even LED curing processes. The synergist can be a tertiary amine compound. In one example, the synergist can be a polymeric amine synergist such as a derivative of aniline and a polyether amine such as Jeffamine® 900. In other examples, the synergist can be trimethylamine, triethanolamine, methyldiethanolamine, phenyldiethanolamine, N,N,N',N'-tetra(hydroxylethyl)ethylenediamine, dimethylaminoethyl acrylate, dimethylaminoethyl methacrylate, ethyl dimethylaminobenzoate, or combinations thereof.

As mentioned, the first or second photo initiator can act as a primary photo initiator in the photo curable ink, or can act as a sensitizer for another photo initiator. Therefore, the photo curable ink can in some cases include a second photo initiator in addition to the photo initiators disclosed herein. Examples of radical photo initiators (either as a primary, secondary, or sensitizer photo initiator) include, by way of illustration and not limitation, 1-hydroxy-cyclohexylphenylketone, benzophenone, 2,4,6-trimethylbenzo-phenone, 4-methylbenzophenone, diphenyl-(2,4,6-trimethylbenzoyl) phosphine oxide, phenyl bis(2, 4,6trimethylbenzoyl)phosphine oxide, 2-hydroxy-2-methyl-1-phenyl-1-propanone, benzyl-dimethyl ketal, 2-methyl-l-[4-(methylthio)phenyl]-2-morpholinopropan-l-one, or combinations thereof. Non-limiting examples of additional photo initiators include alpha amino ketone UV photo initiators such as Ciba® Irgacure® 907, Ciba® Irgacure® 369, and Ciba® Irgacure® 379; bis acylphosphine oxide (BAPO) UV photo initiators such as Irgacure® 819, Darocur® 4265, and Darocur® TPO; alpha hydroxy ketone UV photo initiators such as Irgacure® 184 and Darocur® 1173; including photo initiators with or without sensitizers such as Darocur® ITX (2-isopropyl thioxanthone).

The colorant in the photo curable ink can be a pigment, a dye, or a combination thereof. In some examples, the colorant can be present in an amount from 0.5 wt % to 10 wt % in the photo curable ink. In one example, the colorant can be present in an amount from 1 wt % to 5 wt %. In another example, the colorant can be present in an amount from 5 wt % to 10 wt %.

In some examples, the colorant can be a dye. The dye can be nonionic, cationic, anionic, or a mixture of nonionic, cationic, and/or anionic dyes. Specific examples of dyes that can be used include, but are not limited to, Sulforhodamine B, Acid Blue 113, Acid Blue 29, Acid Red 4, Rose Bengal, Acid Yellow 17, Acid Yellow 29, Acid Yellow 42, Acridine Yellow G, Acid Yellow 23, Acid Blue 9, Nitro Blue Tetrazolium Chloride Monohydrate or Nitro BT, Rhodamine 6G, Rhodamine 123, Rhodamine B, Rhodamine B Isocyanate, Safranine O, Azure B, and Azure B Eosinate, which are available from Sigma-Aldrich Chemical Company (St. Louis, Mo.). Examples of anionic, water-soluble dyes include, but are not limited to, Direct Yellow 132, Direct Blue 199, Magenta 377 (available from Ilford AG, Switzerland), alone or together with Acid Red 52. Examples of water-insoluble dyes include azo, xanthene, methine, polymethine, and anthraquinone dyes. Specific examples of water-insoluble dyes include Orasol® Blue GN, Orasol® Pink, and Orasol® Yellow dyes available from Ciba-Geigy Corp. Black dyes may include, but are not limited to, Direct Black 154, Direct Black 168, Fast Black 2, Direct Black 171, Direct Black 19, Acid Black 1, Acid Black 191, Mobay Black SP, and Acid Black 2.

In other examples, the colorant can be a pigment. The pigment can be self-dispersed with a polymer, oligomer, or small molecule; or can be dispersed with a separate dispersant. Suitable pigments include, but are not limited to, the following pigments available from BASF: Paliogen® Orange, Heliogen® Blue L 6901F, Heliogen® Blue NBD 7010, Heliogen® Blue K 7090, Heliogen® Blue L 7101F, Paliogen® Blue L 6470, Heliogen® Green K 8683, and Heliogen® Green L 9140. The following black pigments are available from Cabot: Monarch® 1400, Monarch® 1300, Monarch® 1100, Monarch® 1000, Monarch® 900, Monarch® 880, Monarch® 800, and Monarch® 700. The following pigments are available from CIBA: Chromophtal® Yellow 3G, Chromophtal® Yellow GR, Chromophtal® Yellow 8G, Igrazin® Yellow 5GT, Igrantee Rubine 4BL, Monastral® Magenta, Monastral® Scarlet, Monastral® Violet R, Monastral® Red B, and Monastral® Violet Maroon B. The following pigments are available from Degussa: Printex® U, Printex® V, Printex® 140U, Printex® 140V, Color Black FW 200, Color Black FW 2, Color Black FW 2V, Color Black FW 1, Color Black FW 18, Color Black S 160, Color Black S 170, Special Black 6, Special Black 5, Special Black 4A, and Special Black 4. The following pigment is available from DuPont: Tipure® R-101. The following pigments are available from Heubach: Dalamar® Yellow YT-858-D and Heucophthal Blue G XBT-583D. The following pigments are available from Clariant: Permanent Yellow GR, Permanent Yellow G, Permanent Yellow DHG, Permanent Yellow NCG-71, Permanent Yellow GG, Hansa Yellow RA, Hansa Brilliant Yellow 5GX-02, Hansa Yellow-X, Novoperm® Yellow HR, Novoperm® Yellow FGL, Hansa Brilliant Yellow 10GX, Permanent Yellow G3R-01, Hostaperm® Yellow H4G, Hostaperm® Yellow H3G, Hostaperm® Orange GR, Hostaperm® Scarlet GO, and Permanent Rubine F6B. The following pigments are available from Mobay: Quindo® Magenta, Indofast® Brilliant Scarlet, Quindo® Red R6700, Quindo® Red R6713, and Indofast® Violet. The following pigments are available from Sun Chemical: L74-1357 Yellow, L75-1331 Yellow, and L75-2577 Yellow. The following pigments are available from Columbian: Raven® 7000, Raven® 5750, Raven® 5250, Raven® 5000, and Raven® 3500. The following pigment is available from Sun Chemical: LHD9303 Black. Any other pigment and/or dye can be used that is useful in modifying the color of the UV curable ink. Additionally, the colorant can include a white pigment such as titanium dioxide, or other inorganic pigments such as zinc oxide and iron oxide.

The components of the photo curable ink can be selected to give the ink good ink jetting performance. Besides the photo curable binder, photo active co-solvents, photo initiator(s), sensitizer, amine synergist, and/or the colorant, the photo curable ink can also include a liquid vehicle. Liquid vehicle formulations that can be used in the photo curable ink can include water and one or more co-solvents (other than the photo active co-solvent) present in total at from 1 wt % to 50 wt %, depending on the jetting architecture.

Classes of co-solvents (in addition to the photo active co-solvent) that can be used can include organic co-solvents including aliphatic alcohols, aromatic alcohols, diols, glycol ethers, polyglycol ethers, caprolactams, formamides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs ($C_6$-$C_{12}$) of polyethylene glycol alkyl ethers, N-alkyl caprolactams, unsubstituted caprolactams, both substituted and unsubstituted formamides, both substituted and unsubstituted acetamides, and the like. Specific examples of solvents that can be used include, but are not limited to, 2-pyrrolidinone, N-methylpyrrolidone, 2-hydroxyethyl-2-pyrrolidone, 2-methyl-1,3-propanediol, tetraethylene glycol, 1,6-hexanediol, 1,5-hexanediol and 1,5-pentanediol.

Further, one or more non-ionic, cationic, and/or anionic surfactant can be present, ranging from 0.01 wt % to 20 wt %. In one example, the surfactant can be present in an amount from 5 wt % to 20 wt %. The liquid vehicle can also include dispersants in an amount from 5 wt % to 20 wt %. Examples of surfactants that can be used include alkyl polyethylene oxides, alkyl phenyl polyethylene oxides, polyethylene oxide block copolymers, acetylenic polyethylene oxides, polyethylene oxide (di)esters, polyethylene oxide amines, protonated polyethylene oxide amines, protonated polyethylene oxide amides, dimethicone copolyols, substituted amine oxides, and the like. The amount of surfactant added to the formulation of this disclosure may range from 0.01 wt % to 20 wt %. Suitable surfactants can include, but are not limited to, liponic esters such as Tergitol™ 15-S-12, Tergitol™ 15-S-7 available from Dow Chemical Company, LEG-1 and LEG-7; Triton™ X-100; Triton™ X-405 available from Dow Chemical Company; LEG-1, and sodium dodecylsulfate.

Consistent with the formulation of this disclosure, various other additives can be employed to optimize the properties of the ink composition for specific applications. Examples of these additives are those added to inhibit the growth of harmful microorganisms. These additives may be biocides, fungicides, and other microbial agents, which are routinely used in ink formulations. Examples of suitable microbial agents include, but are not limited to, NUOSEPT® (Nudex, Inc.), UCARCIDE™ (Union carbide Corp.), VANCIDE® (R.T. Vanderbilt Co.), PROXEL® (ICI America), and combinations thereof.

Sequestering agents, such as EDTA (ethylene diamine tetra acetic acid), may be included to eliminate the deleterious effects of heavy metal impurities, and buffer solutions may be used to control the pH of the ink. From 0.01 wt % to 2 wt %, for example, can be used. Viscosity modifiers and buffers may also be present, as well as other additives to modify properties of the ink as desired. Such additives can be present at from 0.01 wt % to 20 wt %.

The balance of the formulation can be purified water, or other vehicle components such as viscosity modifiers, materials for pH adjustment, preservatives, or the like. In one example, the liquid vehicle can be predominantly water, e.g., more than 50 wt % water.

Table 1 shows the composition of an example of a photo curable ink, e.g., UV LED curable ink, formulation in accordance with the present disclosure. The ink can be formulated by mixing these ingredients or by other formulations. The pH of the ink can then be adjusted. In one example, the ingredients can be stirred for 30 minutes and then aqueous potassium hydroxide can be added to adjust the pH to 7 to 12, or in other examples, from 8 to 10, or about 8.5. It is noted that though water concentrations are listed as "balance," it is understood that the balance of components could included other liquid vehicle components or minor amounts of solids often present in inkjet ink compositions.

TABLE 1

| Component | Weight Percent |
|---|---|
| Photo reactive binder (UV reactive polymer) | 1-20% |
| Photo active co-solvent (sensitizer or photo initiator) | 0.15-5% |
| Photo initiator | 0.05-10 |
| Co-photo initiator | *0-10% |
| Synergist | *0-5% |
| Surfactant | 0-20% |
| Anti-kogation agent | 0-5% |
| Pigment | 0.5-10% |
| Organic Co-solvent (in addition to the photo active co-solvent) | 0.1-50% |
| Water (and any other additives) | balance |

*As noted, when the photo active co-photo initiator is included as a sensitizer, the co-photo initiator is at greater than 0%. When the photo active co-photo initiator is included as a photo initiator, the synergist is at greater than 0%. All three components can likewise be present, e.g., the photo initiator, the co-photo initiator, and the synergist.

The photo curable ink can be used to print on a broad selection of substrates including untreated plastics, flexible as well as rigid, porous substrates such as paper, cardboard, foam board, textile, and others. The ink has a good adhesion on a variety of substrates. The photo curable ink also has a good viscosity, enabling good printing performances and the ability to formulate inks suitable for inkjet application. In some examples, the ink can be formulated for thermal inkjet printing. The photo curable ink composition of the present disclosure provides for high printing speed and is very well suited for a use in digital inkjet printing.

The photo active co-solvents of the present disclosure can be stable in aqueous environments at pH from 7 to 12 or higher. Thus, the photo curable ink can be formulated to have a pH from 7 to 12 or higher. In some examples, the photo curable ink can have a pH of 8 or higher, e.g., 8 to 12 or 8 to 10. In one specific example, the photo curable ink can have a pH of about 8.5.

The photo reactive binder can include polymers or monomers that polymerize or cross-link during the UV curing process. As the binder cures, the photo active co-solvent can become cross-linked therewith.

As mentioned, the present disclosure also extends to a method of making a photo curable ink, as shown generally at FIG. 2. The method includes mixing 210 a photo reactive binder; a photo initiator, a co-photo initiator, a synergist, or combination thereof; a colorant; and a liquid vehicle. The liquid vehicle can include water and an acrylamide-containing photo active co-solvent including a bis-tris propane co-solvent or a polypropylene oxide amine co-solvent reacted with an acryloyl group. The photo curable ink can be UV curable, and in one specific example, UV LED curable. In one example, the method can also include adjusting the pH of the ink to be from 7 to 12. In another example, the method can include adjusting the pH of the ink to from 8 to 10.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, "photo initiator" refers to materials that participate in the initiation of photo polymerization. The photo initiators disclosed herein can be used either as a photo initiator or as a sensitizer for another photo initiator. In some systems, the photo active co-solvent can act as both a photo initiator and a sensitizer.

As used herein, "UV curable" refers to compositions that can be cured by exposure to ultraviolet light from any UV source such as a mercury vapor lamp, UV LED source, or the like. Mercury vapor lamps emit high intensity light at wavelengths from 240 nm to 270 nm and 350 nm to 380 nm. There are also ultraviolet LEDs are available at 365 nm and 395 nm wavelengths, among others. "LED curable" refers to compositions that can be cured either by ultraviolet light from an ultraviolet source, such as an Ultraviolet LED (or UV LED) which emits light at a specific wavelength. The term "photo curable" refers generally to compositions that can be cured by exposure to light from any wavelength suitable for the composition being cured. Typically, the photo curable composition will be UV curable, and in some cases UV LED curable.

As used herein, "liquid vehicle" or "ink vehicle" refers to a liquid fluid in which colorant is placed to form an ink. A wide variety of ink vehicles may be used with the systems and methods of the present disclosure. Such ink vehicles may include a mixture of a variety of different agents, including, surfactants, solvents, co-solvents, anti-kogation agents, buffers, biocides, sequestering agents, viscosity modifiers, surface-active agents, water, etc.

As used herein, "colorant" can include dyes and/or pigments.

As used herein, "dye" refers to compounds or molecules that absorb electromagnetic radiation or certain wavelengths thereof. Dyes can impart a visible color to an ink if the dyes absorb wavelengths in the visible spectrum.

As used herein, "pigment" generally includes pigment colorants, magnetic particles, aluminas, silicas, and/or other ceramics, organo-metallics or other opaque particles, whether or not such particulates impart color. Thus, though the present description primarily exemplifies the use of pigment colorants, the term "pigment" can be used more generally to describe not only pigment colorants, but other pigments such as organometallics, ferrites, ceramics, etc. In one specific example, however, the pigment is a pigment colorant.

As used herein, "ink-jetting" or "jetting" refers to compositions that are ejected from jetting architecture, such as ink-jet architecture. Ink-jet architecture can include thermal or piezo architecture. Additionally, such architecture can be configured to print varying drop sizes such as less than 10 picoliters, less than 20 picoliters, less than 30 picoliters, less than 40 picoliters, less than 50 picoliters, etc.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following illustrates several examples of the present disclosure. However, it is to be understood that the following are only illustrative of the application of the principles of the present disclosure. Numerous modifications and alternative compositions, methods, and systems may be devised without departing from the spirit and scope of the present disclosure. The appended claims are intended to cover such modifications and arrangements.

Example 1

Synthesis of Photoactive Co-Solvent 1

To a solution of bis-tris propane (56.5 g, 0.2 mol) in 200 ml of dry THF in a three-necked round bottom flask with mechanical stir was added trimethylamine (40.52 g, 0.4 mol) at room temperature. The resulting solution was cooled down to 0° C. under $N_2$, then a solution of acryloyl chloride (36.2 g, 0.4 mol) in 100 ml of dry THF was added dropwise at 0° C. After the addition was complete, the mixture was allowed to warm to room temperature and continued to stir at room temperature for overnight. The white solid was collected by filtration and washed with THF (3×50 ml). The combined THF filtrate and THF washing solutions were evaporated off to give a residue. The residue was dissolved into 500 ml of chloroform and washed with saturated sodium bicarbonate aqueous solution (3×100 ml) until no gas generated. The chloroform layer was then dried with sodium sulfate. Sodium sulfate was removed by filtration and the filtrate was evaporated off to give the desired BIS TRIS Propane diacrylamide (BTPDA, Photo Active Co-solvent-1) (50.7 g, 65%).

Example 2

Synthesis of Photoactive Co-Solvent IV

To a solution of Jeffamine® ED 900 (100 g, 0.11 mol) in 250 ml of dry THF in a three-necked round bottom flask with mechanical stir was added trimethylamine (22.66 g, 0.22 mol) at room temperature. The resulting solution was cooled down to 0° C. under $N_2$, and then a solution of acryloyl chloride (19.91 g, 0.22 mol) in 50 ml of dry THF was added dropwise at 0° C. After the addition was complete, the mixture was allowed to warm to room temperature and continued to stir at room temperature overnight. The white solid was collected by filtration and washed with THF (×50 ml). The combined THF filtrate and THF washing solutions were evaporated off to give a residue. The residue was dissolved into 500 ml of chloroform and washed with saturated sodium bicarbonate aqueous solution (×100 ml) until no gas generated. The chloroform layer was then dried with sodium sulfate. Sodium sulfate was removed by filtration and the filtrate was evaporated off to give the desired Jeffamine® 900 diacryloylamide (JA-900 DA) (100 g, 90 wt %).

Example 3

Synthesis of Photoactive Co-Solvent V

To a solution of Jeffamine® T-403 (100 g, 0.2273 mol) in 250 ml of dry THF in a three-necked round bottom flask with mechanical stir was added trimethylamine (70.246 g, 0.682 mol) at room temperature. The resulting solution was cooled down to 0° C. under $N_2$, then a solution of acryloyl chloride (61.7 g, 0.682 mol) in 100 ml of dry THF was added dropwise at 0° C. After the addition was complete, the mixture was allowed to warm to room temperature and continued to stir at room temperature for overnight. The white solid was collected by filtration and washed with THF (×50 ml). The combined THF filtrate and THF washing solutions were evaporated off to give a residue. The residue was dissolved into 500 ml of chloroform and washed with saturated sodium bicarbonate aqueous solution (×100 ml) until no gas generated. The chloroform layer was then dried with sodium sulfate. Sodium sulfate was removed by filtration and the filtrate was evaporated off to give the desired Jeffamine® T-403 triacryloylamide (JA-T-403 TA) (116 g, 85%).

Example 4

Ink Testing Results

Curable water based inks were formulated based on the following formulations found in Table 2:

TABLE 2

| Component of Photo Curable Ink | Wt % |
|---|---|
| Surfynol ® CT-211 (surfactant from Air Products) | 0.8 |
| DX-4000 (fluorosurfactant from Dynax) | 0.5 |
| TPO Na (photo initiator CAS No. 2029-29-1) | 0.5 |
| Irgacure ® 2959 (co-photo initiator from BASF) | 0.25 |
| Irgacure 819 (co-photo initiator from BASF) | 0.2 |
| Thioxanthone derivative of PEG-350 (sensitizer) | 0.25 |
| Photo Curable Polyurethane Dispersion (cPUD—with or without added photoactive co-solvent) | 10 |
| Magenta Pigment (from DIC Corp.) | 4 |
| Water | Balance |

The inks of Table 2 (without photo active co-solvent and with added photo-active solvent) were printed or drawn-down on plastic media and the following tests were performed to evaluate durability: a) Eraser rub at 1 weight (250 g) for 10 cycles; b) Windex rub at 1 weight (250 g) for 5 cycles using a crockmeter cloth; c) Water rub at no weight (0 g) for 1 cycle using a crockmeter cloth; d) 70 wt % isopropyl alcohol (IPA) rub at 1 weight (250 g) for 5 cycles using a crockmeter cloth; and e) Paper clip scratch test. Durability of ink films was evaluated by the following test criteria (visual evaluation): 1-5, where 5 indicates fail (ink is fully removed), and 1 means excellent rub resistance. The durability for each ink is found in Table 3, as follows:

TABLE 3

| Photo Curable Ink | Eraser Rub UV-LED | Windex Rub UV-LED | 70% IPA Rub UV-LED | Water Rub UV-LED | Paper Clip UV-LED |
|---|---|---|---|---|---|
| cPUD | 4 | 4 | 4 | 4 | 5 |
| cPUD with 7 wt % Photo Active Co-solvent IV | 1.5 | 1 | 2 | 1 | 2 |
| cPUD with 5 wt % Photo Active Co-solvent IV | 3 | 2.5 | 3 | 1 | 3 |

As can be seen in Table 3, there is a trend of improvement of durability across the board with the addition of Photo Active Co-solvent IV. The ink film with only the photo curable polyurethane dispersion came close to or failed all of the tests; while adding even 5 wt % of JA900DA improved the durability across the board, especially for the water rub. With 7 wt % of Photo Active Co-solvent IV, all of the durability tests, including the 70 wt % IPA and paper clip scratch test, passed.

Table 4 below provides some of the properties for the inks prepared in accordance with Table 2 above, as well as a comparative ink with added monomer from Sartomer instead of the cPUD component, as follows:

TABLE 4

| | Time and Conditions | Ink with cPUD only | Ink with cPUD + 7 wt % Photo Active Co-solvent IV | Ink with cPUD + 5 wt % Photo Active Co-solvent IV | Ink with Sartomer monomer |
|---|---|---|---|---|---|
| Viscosity (cPs) | T-0 at 25° C. | 2.503 | 3.37 | 3.128 | 4.444 |
| | T-1 week at 50° C. | 2.507 | 3.628 | 3.223 | 4.015 |
| | % Δ | 0.16% | 7.65% | 3.04% | −9.65% |
| Particle Size (nm) | T-0 at 25° C. | 123.3 | 120 | 126 | 4010 |
| | T-1 week at 50° C. | 130.5 | 131 | 131 | 3304 |
| | % Δ | 5.80% | 9.16% | 3.97% | −17.61% |

TABLE 4-continued

|  | Time and Conditions | Ink with cPUD only | Ink with cPUD + 7 wt % Photo Active Co-solvent IV | Ink with cPUD + 5 wt % Photo Active Co-solvent IV | Ink with Sartomer monomer |
|---|---|---|---|---|---|
| pH | T-0 at 25° C. | 9.16 | 8.45 | 8.42 | 8.04 |
|  | T-1 week at 50° C. | 9.05 | 7.93 | 7.93 | 7.14 |
|  | % Δ | 0.11 | 0.52 | 0.49 | 0.9 |

Table 4 demonstrated compatibility of Photo Active Co-solvent IV with other ingredients of the UV-LED curable inks. The ink containing only the cPUD had excellent stability including viscosity, particle size, and pH stability. While adding 5 wt % or 7 wt % of Photo Active Co-solvent, the stability of the inks slightly decreased but still within acceptable range. At the same time, the ink containing the commercial monomer from Sartomer had poor stability, especially with respect to particle size and pH drop.

Table 5 below provides further detail with respect to Eraser Rub, Windex Rub, Water Rub, and Paper Clip scratch testing as it relates to addition of 7 wt % Photo Active Co-solvent IV to ink. In this example, a score of 5 is considered to be failing, whereas 2 or lower is considered to be acceptable. In this example, a slightly different cPUD was used. In these examples, a draw down application method was used, and no fixer was applied. The inks, as before, were the magenta inks of Table 2, and the inks were applied to SAV

TABLE 5

| Photo Curable Ink | Cured? | Eraser Rub | Windex Rub | Water Rub | Paper Clip |
|---|---|---|---|---|---|
| cPUD | No | 5 | 4 | 4 | 5 |
|  | Yes | 2 | 0.5 | 0.5 | 5 |
| cPUD with cPUD + 7 wt % Photo Active Co-solvent IV | No | 5 | 4 | 4 | 5 |
|  | Yes | 1 | 1 | 1 | 2 |

As can be seen, after curing in the presence of the Photo Active Co-solvent, the Eraser Rub, the Windex Rub, and the Water Rub remained very good, but the Paper Clip Scratch test was far superior compared to the cPUD only inks.

While the present technology has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:

1. An acrylamide-containing photo active co-solvent, comprising a bis-tris propane co-solvent modified with an acryloyl group to form the acrylamide-containing photo active co-solvent, wherein the acrylamide-containing photo active co-solvent has the following structure:

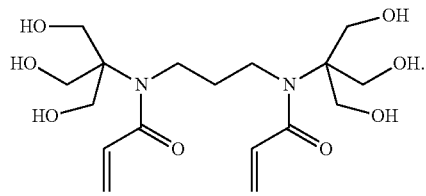 [SMILES: C=CC(=O)N(CCCN(C(=O)C=C)C(CO)(CO)CO)C(CO)(CO)CO]

2. A photo curable ink, comprising:
a photo reactive binder;
a photo initiator;
a co-photo initiator, a synergist, or combination thereof;
a colorant; and
a liquid vehicle including water and a bis-tris propane co-solvent modified with an acryloyl group to form an acrylamide-containing photo active co-solvent, wherein the acrylamide-containing photo active co-solvent has the following structure:

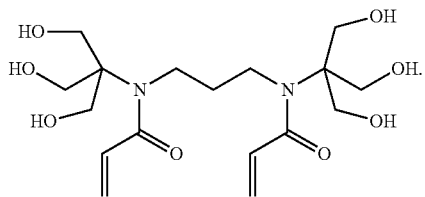 [SMILES: C=CC(=O)N(CCCN(C(=O)C=C)C(CO)(CO)CO)C(CO)(CO)CO]

3. A method of preparing a photo curable ink, comprising mixing a photo reactive binder; a photo initiator; a co-photo initiator, a synergist, or combination thereof; a colorant; and a liquid vehicle, wherein the liquid vehicle includes water an acrylamide-containing photo active co-solvent comprising a bis-tris propane co-solvent modified with an acryloyl group to form an acrylamide-containing photo active co-solvent, wherein the acrylamide-containing photo active co-solvent has the following structure:

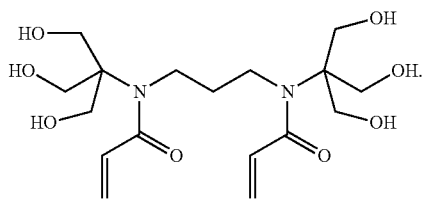 [SMILES: C=CC(=O)N(CCCN(C(=O)C=C)C(CO)(CO)CO)C(CO)(CO)CO]

4. The photo curable ink of claim 2, wherein the photo reactive binder includes a UV or LED curable polyurethane, a hydrophobic radiation-curable monomer, or a water dispersible (meth)acrylated polyurethane.

5. The photo curable ink of claim 2, wherein the photo initiator is a Type I photo initiator.

6. The photo curable ink of claim 2, wherein the photo initiator is a Type II photo initiator.

7. The photo curable ink of claim 2, wherein the co-photo initiator is present in the photo curable ink.

8. The photo curable ink of claim 2, wherein the synergist is present in the photo curable ink.

9. The photo curable ink of claim 8, wherein the synergist is an amine synergist selected from trimethylamine, triethanolamine, methyldiethanolamine, phenyldiethanolamine, N,N,N',N'-tetra(hydroxylethyl)ethylenediamine, dimethylaminoethyl acrylate, dimethylaminoethyl methacrylate, ethyl dimethylaminobenzoate, or a combination thereof.

10. The photo curable ink of claim 2, wherein the photo initiator includes a radical photo initiator selected 1-hydroxy-cyclohexylphenylketone, benzophenone, 2,4,6-trimethylbenzo-phenone, 4-methylbenzophenone, diphenyl-(2,4,6-trimethylbenzoyl)phosphine oxide, phenyl bis(2,4,6trimethylbenzoyl)phosphine oxide, 2-hydroxy-2-methyl-1-phenyl-1-propanone, benzyl-dimethyl ketal, 2-methyl-1-[4-(methylthio)phenyl]-2-morpholinopropan-1-one, alpha amino ketone, bis acylphosphine oxide (BAPO), alpha hydroxy ketone, or a combination thereof.

11. The photo curable ink of claim 2, wherein the colorant includes a pigment.

12. The method of claim 3, wherein the photo reactive binder includes a UV or LED curable polyurethane, a hydrophobic radiation-curable monomer, or a water dispersible (meth)acrylated polyurethane.

13. The method of claim 3, wherein the photo initiator is a Type I photo initiator.

14. The method of claim 3, wherein the photo initiator is a Type II photo initiator.

15. The method of claim 3, wherein the co-photo initiator is present in the photo curable ink.

16. The method of claim 3, wherein the synergist is present in the photo curable ink.

17. The method of claim 3, wherein the synergist is an amine synergist selected from trimethylamine, triethanolamine, methyldiethanolamine, phenyldiethanolamine, N,N,N',N'-tetra(hydroxyethyl)ethylenediamine, dimethylaminoethyl acrylate, dimethylaminoethyl methacrylate, ethyl dimethylaminobenzoate, or a combination thereof.

18. The method of claim 3, wherein the photo initiator includes a radical photo initiator selected 1-hydroxy-cyclohexylphenylketone, benzophenone, 2,4,6-trimethylbenzophenone, 4-methylbenzophenone, diphenyl-(2,4,6-trimethylbenzoyl)phosphine oxide, phenyl bis(2,4,6trimethylbenzoyl)phosphine oxide, 2-hydroxy-2-methyl-1-phenyl-1-propanone, benzyl-dimethyl ketal, 2-methyl-1-[4-(methylthio)phenyl]-2-morpholinopropan-1-one, alpha amino ketone, bis acylphosphine oxide (BAPO), alpha hydroxy ketone, or a combination thereof.

19. The method of claim 3, wherein the colorant includes a pigment.

* * * * *